(12) United States Patent
DiMatteo et al.

(10) Patent No.: US 7,682,382 B2
(45) Date of Patent: *Mar. 23, 2010

(54) INTRALUMINAL LINING

(75) Inventors: Kristian DiMatteo, Watertown, MA (US); Adrian Ravenscroft, Milton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 119 days.

This patent is subject to a terminal disclaimer.

(21) Appl. No.: 11/396,970

(22) Filed: Apr. 3, 2006

(65) Prior Publication Data

US 2006/0195173 A1 Aug. 31, 2006

Related U.S. Application Data

(63) Continuation of application No. 10/342,914, filed on Jan. 15, 2003, now Pat. No. 7,060,087, which is a continuation of application No. 09/957,618, filed on Sep. 20, 2001, now Pat. No. 6,514,283, which is a continuation of application No. 09/283,556, filed on Apr. 1, 1999, now Pat. No. 6,312,457.

(51) Int. Cl.
*A61F 2/06* (2006.01)
(52) U.S. Cl. .................................................. 623/1.13
(58) Field of Classification Search ......... 623/1.1–1.54; 606/190, 191, 194, 198, 200
See application file for complete search history.

(56) References Cited

U.S. PATENT DOCUMENTS

| | | | |
|---|---|---|---|
| 4,577,631 A | 3/1986 | Kreamer | |
| 4,629,458 A | 12/1986 | Pinchuk | |
| 4,699,146 A | 10/1987 | Sieverding | |
| 4,877,030 A | 10/1989 | Beck et al. | |
| 4,878,908 A | 11/1989 | Martin et al. | |
| 5,035,894 A | 7/1991 | Lee et al. | |
| 5,100,429 A | 3/1992 | Sinofsky et al. | |
| 5,628,782 A | 5/1997 | Myers et al. | |
| 5,628,788 A | 5/1997 | Pinchuk | |
| 5,670,161 A | 9/1997 | Healy et al. | |
| 5,693,085 A | 12/1997 | Buirge et al. | |
| 5,735,892 A * | 4/1998 | Myers et al. ............... | 623/1.13 |
| 5,735,896 A | 4/1998 | Amon et al. | |
| 5,749,880 A | 5/1998 | Banas et al. | |
| 5,755,775 A * | 5/1998 | Trerotola et al. ............. | 606/194 |
| 5,755,778 A * | 5/1998 | Kleshinski .................. | 623/1.13 |
| 5,769,882 A | 6/1998 | Fogarty et al. | |
| 5,769,884 A | 6/1998 | Solovay | |
| 5,810,721 A | 9/1998 | Mueller et al. | |

(Continued)

FOREIGN PATENT DOCUMENTS

EP 0 566 245 A1 10/1993

(Continued)

*Primary Examiner*—Ralph A Lewis
(74) *Attorney, Agent, or Firm*—Vidas, Arrett & Steinkraus

(57) ABSTRACT

The present invention is directed to a prosthesis for implantation within a body lumen. The prosthesis includes a biocompatible elongate intraluminal liner in the form of a graft, with a biocompatible adhesive being disposed on an exterior surface of the graft. The adhesive is active in an intraluminal environment so as to bond the exterior surface of the graft to an intraluminal surface of said body lumen, such as the interior of a blood vessel.

17 Claims, 4 Drawing Sheets

U.S. PATENT DOCUMENTS

| | | |
|---|---|---|
| 5,824,054 A | 10/1998 | Khosravi et al. |
| 5,984,963 A | 11/1999 | Ryan et al. |
| 6,165,212 A * | 12/2000 | Dereume et al. ............ 623/1.13 |
| 6,312,457 B1 * | 11/2001 | DiMatteo et al. ............ 623/1.13 |
| 6,514,283 B2 * | 2/2003 | DiMatteo et al. ............ 623/1.13 |
| 6,626,939 B1 * | 9/2003 | Burnside et al. ............ 623/1.38 |
| 7,060,087 B2 * | 6/2006 | DiMatteo et al. ............ 623/1.13 |

FOREIGN PATENT DOCUMENTS

| | | |
|---|---|---|
| EP | 0 698 396 A1 | 2/1996 |
| WO | WO 91/17744 | 11/1991 |

* cited by examiner

INTRALUMINAL LINING

CROSS-REFERENCE TO RELATED APPLICATION

The present application is a continuation of U.S. application Ser. No. 10/342,914, filed on Jan. 15, 2003 now U.S. Pat. No. 7,060,087, which is a continuation of U.S. application Ser. No. 09/957,618, filed Sep. 20, 2001, now U.S. Pat. No. 6,514,283, issued Feb. 4, 2003; which is a continuation of U.S. application Ser. No. 09/283,556, filed Apr. 1, 1999, now U.S. Pat. No. 6,312,457, issued Nov. 6, 2001, the contents of all of which are incorporated herein by reference.

FIELD OF THE INVENTION

The present invention relates to the field of intraluminal prostheses. More specifically, the present invention is directed to an intraluminal prosthesis which is adhesively bonded to the interior wall of a body conduit.

BACKGROUND OF THE INVENTION

The use of tubular devices or conduits is well known in the repair or replacement of damaged or diseased lumens within the body. For example, tubular conduits are used to repair lumens such as in the esophagus and colon areas, and in particular, prostheses are used in the vascular system to repair, buttress or replace a weakened section of the vessel. It is well known in the field of vascular surgery to surgically replace a portion of a vessel with an endoprosthesis, such as a vascular graft. Such replacement procedures, however, generally involve invasive surgery, resulting in extensive recovery and high risk of infection and/or rejection.

More recently, the general trend in vascular surgery has moved toward less invasive techniques for repair of vessels. In order to minimize the recovery period and reduce the risk of infection and/or rejection, procedures have been developed for delivery and implantation of endoprostheses using minimally invasive procedures. Commonly, such procedures include intraluminal delivery involving percutaneous insertion of an endoprosthesis by way of a delivery catheter. Such endoprostheses include grafts which are generally in the form of a tubular lining provided for delivery within a section of a body conduit to treat the complications of atherosclerosis, i.e. arterial occlusion or aneurysms. These less invasive procedures permit delivery and implementation of an endoprosthesis without the need for replacement of a portion of the vessel, and thus eliminate major surgical intervention and the risks associated therewith. In order to secure a graft in place after delivery, it is common practice to employ a variety of mechanical securement means, for example sutures, staples and the like. Additionally, it is well known to employ a stent in combination with a graft in order to support and secure the graft in place within the body passageway after implantation. Stents are typically radially expandable and/or contractible support members which are positioned within a graft member or other tubular prosthesis. In common usage, after a prosthesis has been properly positioned, the stent is expanded to anchor the prosthesis within the body passageway. Natural cell growth through the wall of the prosthesis can then further anchor the prosthesis in place within the body lumen.

As can be appreciated, such mechanical securement means cannot effectively secure an endoprosthesis such as a graft continuously along the entire length thereof. Such mechanical securement can result in unsecured portions of the graft, thus resulting in gaps between the graft wall and the intraluminal wall of the vessel. Such gaps can result in an increased amount of cell growth necessary to anchor the prosthesis in place. Further, such mechanical securement can result in a bulky structure present within the lumen, which can inhibit normal flow through the lumen, and create a site for occlusion within the vessel.

Moreover, in recent years, polytetrafluoroethylene (PTFE) has become increasingly popular for use in such vascular graft applications due to its non-stick and inert properties. As can be appreciated, however, PTFE is difficult to adhere to vessel walls due to these inert properties.

Accordingly, a need exists for an implantable prosthesis which can be easily delivered to a repair site within a vessel, and can be effectively secured to the internal wall surface of the vessel along the length of the prosthesis to limit the gap between the prosthesis and the vessel wall.

SUMMARY OF THE INVENTION

It is an object of the present invention to provide an implantable prosthesis capable of effective securement within a body lumen.

It is a further object of the present invention to provide an implantable prosthesis which does not inhibit normal flow through the lumen.

These and other objects are attained through the present invention involving a prosthesis for implantation within a body lumen. The prosthesis includes a biocompatible elongate intraluminal liner having an interior surface and an exterior surface. A biocompatible adhesive is disposed on the exterior surface of the liner. The adhesive is active in an intraluminal environment so as to bond the exterior surface of the liner to an intraluminal surface of the body lumen.

The adhesive may be any type of adhesive known in the art which is capable of bonding in an intraluminal environment. Preferably, the adhesive is bioabsorbable, and may be a curable polymer adhesive such as photodynamically cured adhesives including ultraviolet light, temperature curing adhesives, or may be pressure sensitive adhesive. Particularly preferred adhesives include those selected from the group consisting of polyurethanes, cyanoacrylates, silicones, (meth)acrylates, and combinations thereof. The adhesive may also be a biological sealant capable of bonding the liner to the intraluminal surface, including biological sealants selected from the group consisting of fibrin, collagen, poly(L-glutamic acid), gelatin based hydrogel, N-vinyl pyrrolidone, and mixtures and combinations thereof.

In an alternate embodiment of the present invention, the adhesive is held within frangible encapsulants or nodules which are disposed on the exterior surface of the tubular body. The encapsulants are capable of rupturing when compressed between the tubular body and the lumen so as to release the adhesive, thereby bonding the exterior surface of the said liner to an intraluminal surface of the body lumen.

The liner preferably includes a plurality of pores sufficient to permit the ingrowth of body tissue. The adhesive may be disposed through at least one of these pores in the liner. Further, a mechanical support such as a radially expandable stent may be disposed along the interior surface of the tubular body to maintain the tubular body in an open position. The mechanical support may be removable from the tubular body, and may be bioabsorbable. The mechanical support may be any type of support known, such as porous polymeric band or a helically wound wire. Preferably, the mechanical support is positioned within at least one longitudinal end of the tubular body, most preferably at an upstream end of the tubular body, and may be provided at both longitudinal ends of the tubular body. The adhesive may extend through the pores of the liner and bond the mechanical support to the liner.

The liner may be in the form of a woven, knitted or braided textile tubular body, a spun filament tubular body, an extruded tube, or may be formed from a polymeric sheet. Preferably, the tubular body is formed from a material selected from the group consisting of polyesters, polypropylenes, polyethylenes, polyurethanes, polytetrafluoroethylenes, poly-alpha-hydroxy-acids, and combinations thereof. The liner may be a bioabsorbable material, but is more preferentially a biologically inert material, such as polytetrafluoroethylene (PTFE). The liner may expandable from an insertion diameter to an implantation diameter which is greater than the insertion diameter so that at the implantation diameter the liner is conformable to the intraluminal surface of the body lumen.

In alternate embodiments, the prosthesis further includes a removable cover over the adhesive for delivery, and may include a concentric tubular body within the liner. In such embodiments, the mechanical support is preferably positioned between the concentric tubular body and the liner.

In a further embodiment of the present invention, a method of adhering an intraluminal liner to a venal wall is provided. The method includes providing a prosthesis including an intraluminal liner having a biocompatible adhesive active in an intraluminal environment disposed on an exterior surface thereof; delivering the prosthesis to an area of implantation; and expanding the prosthesis so as to cause the adhesive to contact an interior surface of the venal wall, thereby causing the adhesive to bond the prosthesis to the venal wall.

DETAILED DESCRIPTION OF THE PREFERRED EMBODIMENT

The present invention is directed to a prosthesis for implantation within a body lumen. The prosthesis includes a biocompatible elongate intraluminal liner in the form of a graft, with a biocompatible adhesive being disposed on an exterior surface of the graft. The adhesive is active in an intraluminal environment so as to bond the exterior surface of the graft to an intraluminal surface of the body lumen, such as the interior of a blood vessel. Typically, implantable prostheses such as vascular grafts are held in place within a body lumen by suturing or by anchoring with a mechanical device such as a stent. With the present invention, prostheses can be properly anchored in place within a body lumen and maintain the vessel from occluding without the need for such suturing or mechanical supports, thus reducing the possibility of thrombus formation and neo-intimal hyperplasia.

Figure 1:
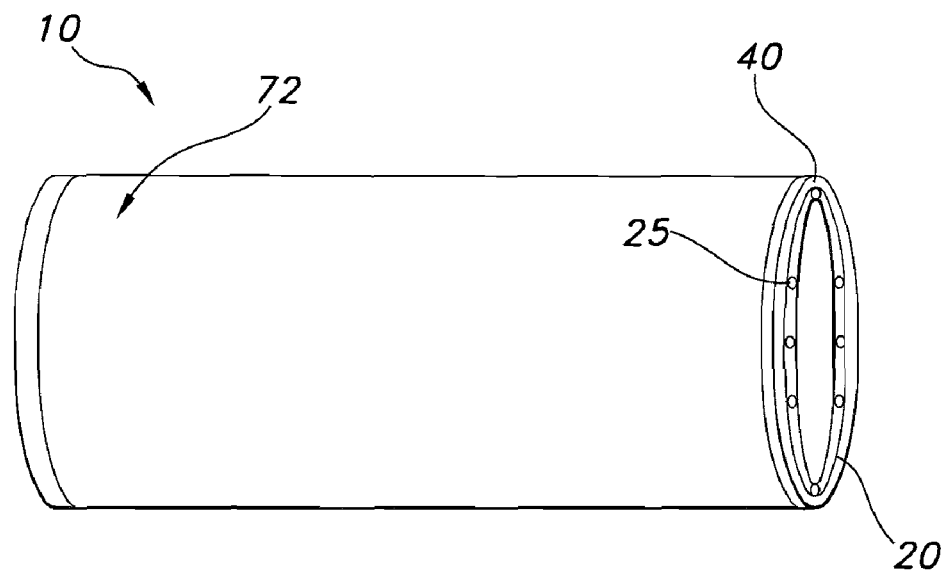
FIG. 1 depicts a perspective view of a prosthesis according to the present invention.

With reference to the drawings, FIG. 1 depicts a prosthesis according to the present invention. Prosthesis 10 includes intraluminal liner 20 and biocompatible adhesive 40. Intraluminal liner 20 is defined by an elongate tubular body 21, including internal surface 23 and external surface 24.

Intraluminal liner 20 is preferably in the form of a graft, such as a vascular graft for repair and/or replacement of damaged or diseased blood vessels. As such, intraluminal liner 20 is constructed of any material and in any manner known in the art. For example, intraluminal liner 20 may be constructed of an elastomeric material, a bioabsorbable material, a shape-memory material, and the like. Intraluminal liner 20 may be constructed of spun fibers or filaments such as electrostatically spun filaments, or may be constructed of a textile material, such as a woven, knitted and/or braided textile material commonly used as implantable tubular prostheses. Such a textile prosthesis is preferably constructed of yarns or fibers which are interlaced to form a textile tubular fabric. The yarns or fibers can be selected from any known biocompatible material, for example, synthetic materials such as thermoplastic polymers including polyesters, polypropylenes, polyethylenes, polyurethanes, polytetrafluoroethylenes, and mixtures thereof. The yarns of the textile material of tubular body 21 may be of the monofilament, multifilament, or spun type, and may be flat, twisted or textured, and may have high, low or moderate shrinkage properties. Additionally, the yarn type and yarn denier can be selected to meet specific properties for the prosthesis, such as porosity, flexibility and compliance.

Tubular body 21 of intraluminal liner 20 may also be constructed from a bioabsorbable material, for example as a shaped or molded tubular body 21, or as a textile or spun tubular body. A non-limiting list of suitable absorbable materials includes poly-caprolactone (PCL) and poly-alpha-hydroxy-acids, such as poly-L-lactide (PLLA), poly-D-lactide (PDLA) and poly-glycolide (PGA), or mixtures thereof.

Tubular body 21 of intraluminal liner 20 may also be constructed of a polymeric material, such as a thermoplastic polymer. For example, tubular body 21 of intraluminal liner 20 may be a molded tubular structure, an extruded polymer tube, or may be a polymeric sheet wrapped and formed into a tubular configuration. Examples of suitable materials are thermoplastic polymers including polyesters, polypropylenes, polyethylenes, polyurethanes, polytetrafluoroethylenes, and mixtures thereof. Any known processing of the thus constructed tubular body 21 may further be undertaken to impart specific characteristics to tubular body 21, such as expanding, stretching, orienting, heat setting or conditioning, and the like. Desirably, tubular body 21 is an extruded polytetrafluoroethylene (PTFE) tube which has been expanded and heat set. Such a PTFE tube may be balloon expanded prior to attachment to the balloon, may be balloon expanded in vivo, or may be stent expanded by an internal stent in vivo.

Preferably, intraluminal liner 20 is porous or microporous, most preferably such that tubular body 21 includes pores extending throughout the tubular structure, such as from internal surface 23 to external surface 24. Such pores permit ingrowth of cells therethrough to assist in anchoring prosthesis 10 within a body lumen after implantation. In embodiments including tubular body 21 as a textile material, such porosity is achieved through the interlaced yarns or fibers which form tubular body 21 of intraluminal liner 20. In embodiments including tubular body 21 as a polymeric structure such as a molded tube, an extruded tube or polymeric sheet material, such porosity may be achieved in any known manner, for example by expanding polytetrafluoroethylene to achieve a microporous node and fibril structure, or by including a leachable substance within the polymeric material during construction of the tube, and then leaching the substance from the tube to form a porous structure.

Figure 2:
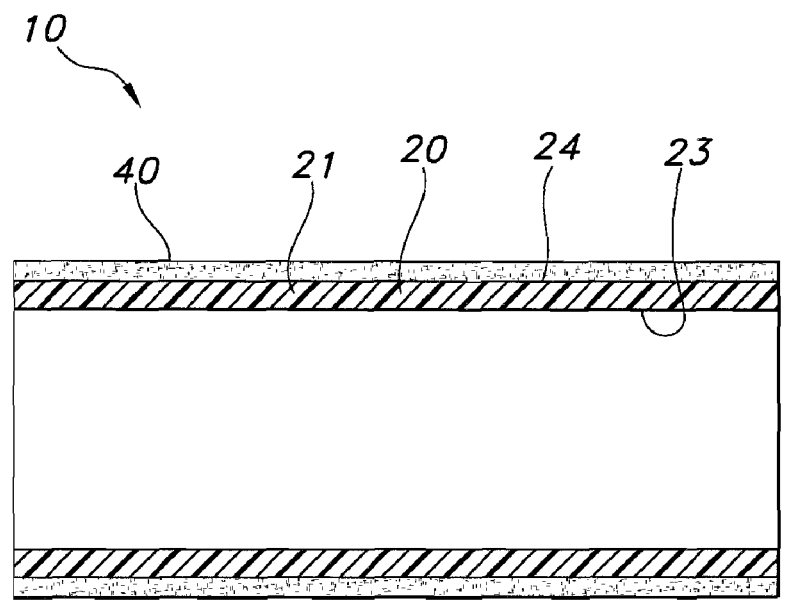
FIG. 2 depicts a cross-sectional view of a prosthesis according to the present invention.

As seen in FIGS. 1 and 2, intraluminal liner 20 includes a biocompatible adhesive 40 disposed on exterior surface 24 of tubular body 21 thereof. Adhesive 40 may be any adhesive active in an intraluminal environment and capable of adhering intraluminal liner 20 to the intraluminal surface of a body lumen, such as a blood vessel. Adhesive 40 is capable of exhibiting adhesive properties in an intraluminal environment so as to bond exterior surface 24 of tubular body 21 to the intraluminal surface of the body lumen. Adhesive 40 may be any composition known for use in connection within the mammalian body. Adhesive 40 may be an adhesive in which adhesive properties activate when positioned within an intraluminal environment, such as when placed in contact with blood. Adhesive 40 may be a pressure sensitive adhesive, wherein the adhesive is activated upon application of pressure of tubular body 21 against an intraluminal surface. Adhesive 40 may also be a curable polymer adhesive for use in the body, such as a photodynamically curing adhesive including ultraviolet light curing adhesives, or a temperature curing adhesive such as heat curing adhesives. In preferred embodiments, adhesive 40 is bioabsorbable, such that adhesive 40 is present during implantation of the prosthesis, and is gradually absorbed into the body over time after the prosthesis has been anchored to the vessel through tissue ingrowth.

Non-limiting examples of suitable adhesives for use in the present invention include polyurethanes, cyanoacrylates, (meth)acrylates, silicones, and combinations and mixtures thereof.

Adhesive 40 may also be a biological sealant, or bio-sealant. Biological sealants refer to tissue adhesives or biological glues. Non-limiting examples of suitable biological sealants include fibrin, collagen, fibrin-collagen combinations, poly (1-glumatic acid), hydrogels such as gelatin based hydrogel, N-vinyl pyrrolidone, and mixtures and combinations thereof.

Adhesive 40 may be provided on the exterior surface 24 of tubular body 21 by any known method, for example by spray coating, dip coating, transfer from a tape, and the like. Adhesive 40 may be provided both longitudinally along the length and circumferentially about tubular body 21. The amount of adhesive 40 disposed on exterior surface 24 of tubular body 21 may vary depending on the characteristics of the adhesive as well as the area of implantation. Adhesive 40 may be disposed on exterior surface 24 of tubular body 21 in a continuous thickness over the entire length thereof, as depicted in the cross-sectional view shown in FIG. 2. Alternatively, adhesive 40 may be provided in varying thicknesses along the length of tubular body 21. In preferred embodiments incorporating a porous tubular body 21, adhesive 40 covers the entire exterior surface 24 of tubular body 21 when prosthesis 10 is in a reduced, implantable diameter, and is provided over a percentage of the outer surface of tubular body 21 after expansion of prosthesis 10 at the site of implantation, such that tubular body 21 remains porous after implantation to permit sufficient tissue ingrowth.

Figure 4:
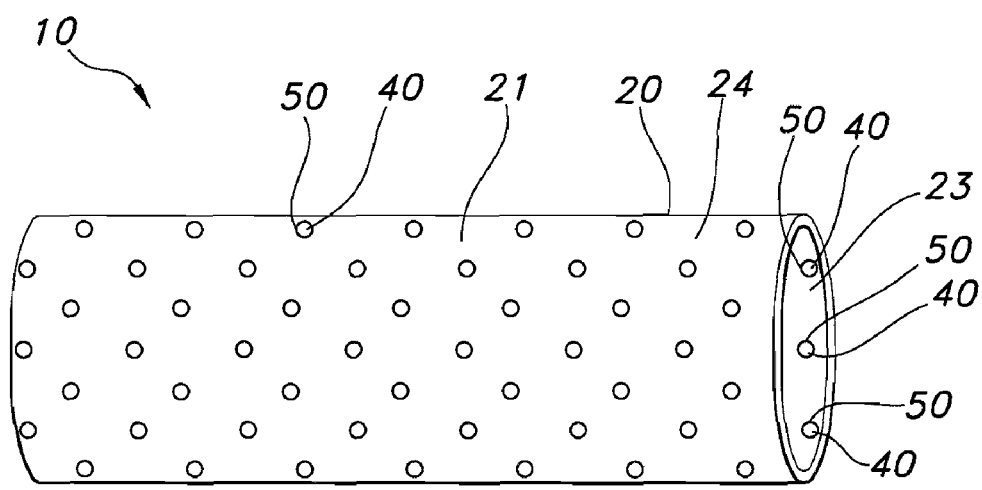
FIG. 4 depicts a perspective view of a prosthesis according to an alternate embodiment of the present invention.
Figure 5A:
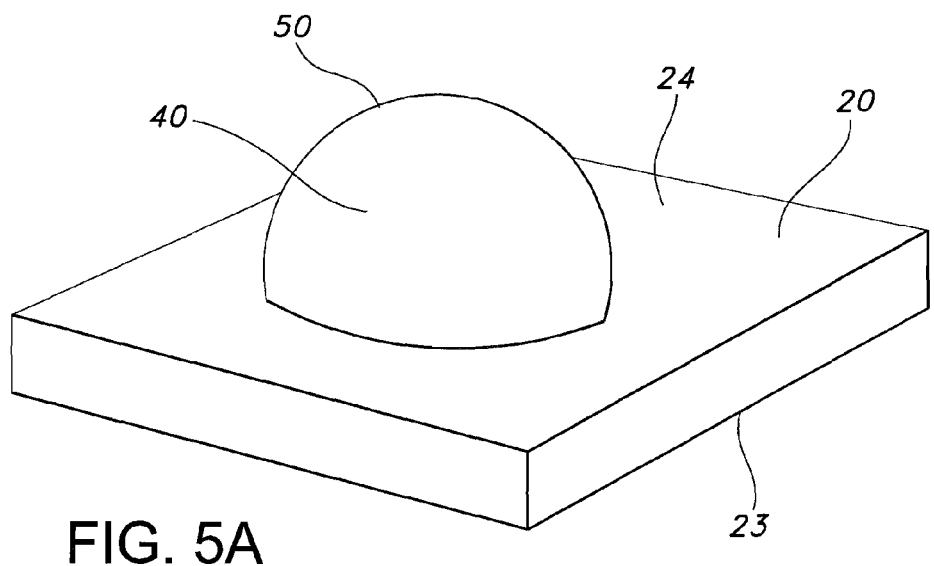
FIGS. 5a and 5b depict enlarged views of the embodiment shown in FIG. 4.

In an alternate embodiment of the present invention, adhesive 40 may be held within frangible encapsulants such as nodules 50 depicted in FIG. 4. Nodules 50, as shown in an enlarged view in FIG. 5a, are disposed on exterior surface 24 of tubular body 21, and are capable of rupturing when compressed between tubular body 21 and the intraluminal surface within the body lumen. Upon rupturing of nodules 50, adhesive 40 is released therefrom, thus bonding intraluminal liner 20 to the intraluminal surface of the body lumen. Nodules 55 are provided on external surface 24 of tubular body 21 in any pattern capable of providing an effective amount of adhesive 40 over the surface of intraluminal lining 20 for bonding with the intraluminal surface of the body lumen upon rupturing of nodules 50. Preferably, nodules 55 are present in a consistent, spaced-apart pattern extending about external surface 24 of tubular body 21, as depicted in FIG. 4.

Nodules 50 are preferably formed on tubular body 21 by suspending the adhesive in a solvent solution, which can then be applied to the surface of the material, for example by spray coating techniques. Nodules 50 may further contain an additional material or composition. For example, in addition to adhesive 40, nodule 50 may contain an antithrombus material; an anticoagulant such as heparin; an anti-inflammatory composition such as dexamethasone, doxorubicin or the like; an enzyme inhibitor such as urokinase or streptokinase or the like; growth factors such as vascular endothelial growth factor (VEGF) or the like, or any other active or additional material.

Figure 5B:
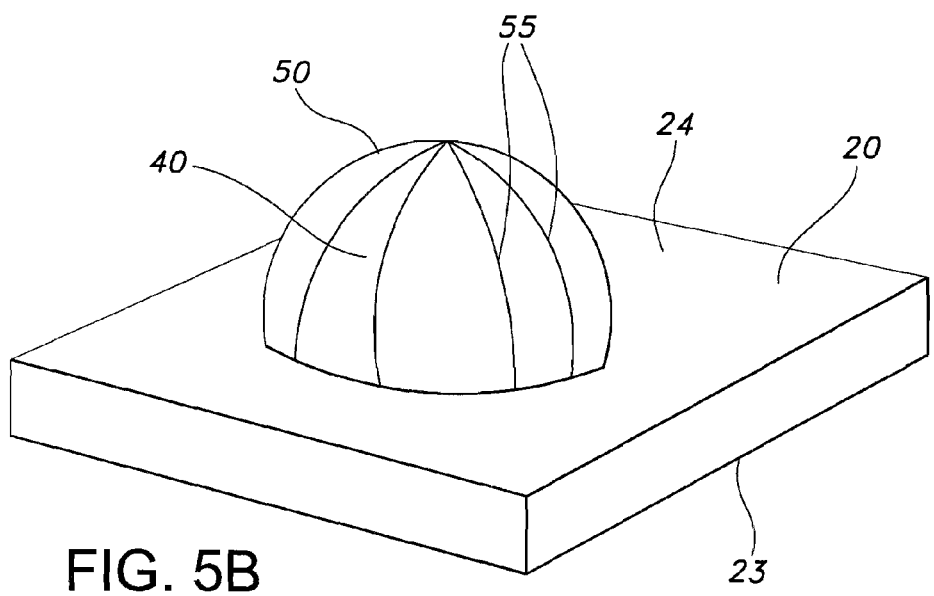

Nodules 50 may further include rupture lines 55 in the surface of nodules 50, as depicted in FIG. 5b. Rupture lines 55 are provided as a series of perforations or tear lines in the surface of nodule 50, thereby providing for a consistent and predetermined rupture pattern of nodules 50.

As indicated above, intraluminal liner 20 is preferably a porous structure, including pores 25 extending through the wall of tubular body 21, as seen in FIG. 1. Such porous structures are well known in the art. For example, it is well known to provide vascular grafts with porous walls for permitting tissue ingrowth through the body of a graft, which assists in anchoring the graft in place within the body. In preferred embodiments, intraluminal liner 20 is constructed of expanded polytetrafluoroethylene (ePTFE) which has been extruded or wrapped into a tubular configuration. Such an ePTFE structure typically includes nodes extending between interconnected fibrils, wherein the nodes form a microporous structure, for example, for permitting such tissue ingrowth.

In particularly preferred embodiments, intraluminal liner 20 includes pores 25 extending through tubular body 21, and adhesive 40 is disposed within such pores 25. In this manner, adhesive 40 provides for further support in adhering intraluminal liner 20 within the body lumen. Such an embodiment is particularly useful when intraluminal liner is constructed of polytetrafluoroethylene. For example, chemical bonding of PTFE is typically difficult with adhesives, due to the inert characteristics of PTFE. By providing a porous or microporous structure with adhesive 40 disposed within pores 25, intraluminal lining 20 can be effectively anchored through a mechanical attachment as well as a chemical attachment, due to the additional surface area and forces provided from adhesive 40 extending through pores 25. In such embodiments, adhesive 40 may be present in an amount to fill all of the pores within tubular body 21 of intraluminal liner 20, or may be present to partially or completely fill only a portion of the pores within tubular body 21 of intraluminal liner 20.

Figure 3A:
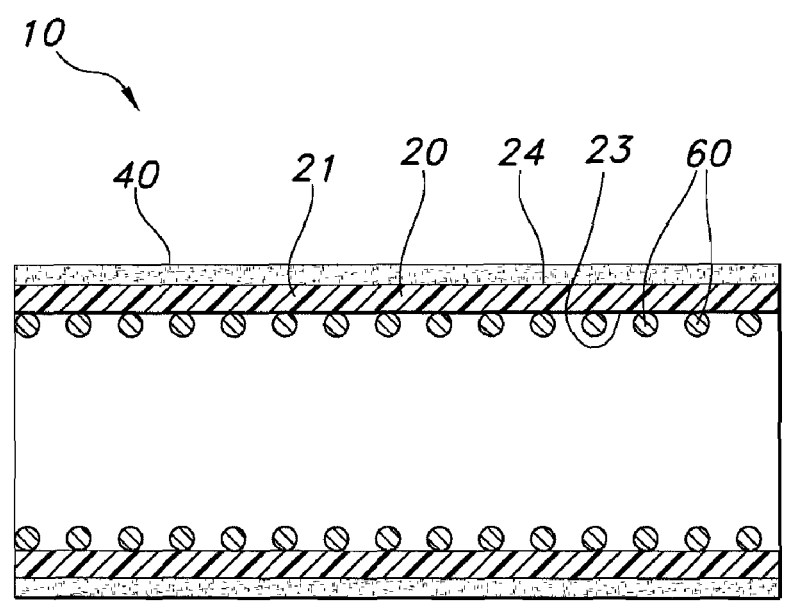
FIGS. 3a, 3b and 3c depict cross-sectional views of various embodiments of a prosthesis of the present invention further including a mechanical support member.
Figure 3B:
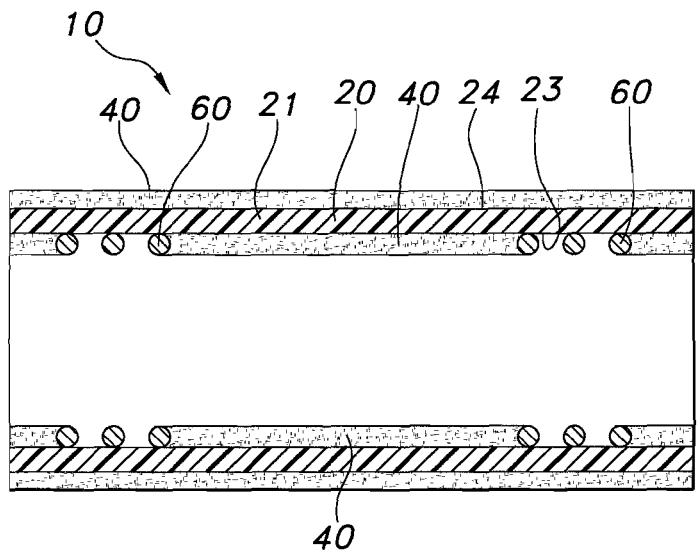
Figure 3C:
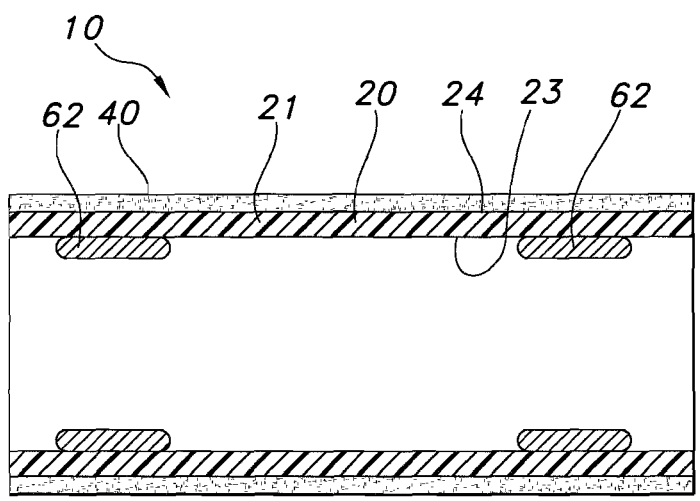

Additionally, prosthesis 10 may include a mechanical support disposed within interior surface 23 of tubular body 21, for further maintaining intraluminal liner 20 in an open position during and after implantation. Such mechanical support is preferably in the form of a stent 60, as depicted in FIGS. 3a, 3b and 3c. Stent 60 may be any type of stent known in the art. Stent 60 is a bio-compatible material, and may be constructed of any material known in the art. For example, stent 60 may be constructed of metal, for example, stainless steel, platinum, gold, nitinol, tantalum, Elgiloy®, and mixtures and alloys thereof. Stent 60 may alternatively be constructed of a polymeric material, such as a thermoplastic material, or of a shape memory material, such as nitinol, as is known in the art. Further, the stent 60 itself may be a porous material to permit tissue ingrowth, as discussed above with respect to intraluminal liner 20. Stent 60 may be removable from prosthesis 10 after implantation, or may be a bioabsorbable material which is gradually absorbed by the body over time, thus leaving intraluminal liner 20 implanted within the body lumen. Alternatively, stent 60 may indefinitely remain positioned within intraluminal liner after implantation of prosthesis 10.

Stent 60 may be constructed in any known shape or form, such as a wire which is wound, for example, in a helical winding to create a tubular structure. Stent 60 may also be constructed of a sheet of material which is wrapped into a tubular structure. Stent 60 may also be constructed of a consistent tube of material, such as tubular band 62, as depicted in FIG. 3c. The mechanical support may include a single stent 60 extending along the entire internal surface or only a portion of internal surface of tubular body 21 of prosthesis 10, such as at one longitudinal end of prosthesis 10. Alternatively, the mechanical support may include multiple stents 60 positioned within the internal surface of tubular body 21 of prosthesis 10, such as two stents 60 positioned at both longitudinal ends of prosthesis 10, as shown in FIGS. 3b and 3c.

In preferred embodiments, stent 60 is radially expandable, such as a self-expandable or a balloon-expandable stent. Such radially expandable stents are well known in the art, and are particular useful in percutaneous delivery applications where the stent can be delivered to the area of implantation at a reduced diameter, and then expanded to maintain and support a vessel once the prosthesis is at the area of implantation. In preferred embodiments incorporating nodules 50 for containing adhesive 40 as discussed above, prosthesis 10 preferably includes stent 60 as a balloon expandable stent, as will be discussed in more detail herein with respect to use of prosthesis 10.

In particularly preferred embodiments, adhesive 40 extends through pores 25 of tubular body 21 of intraluminal liner 20 and bonds stent 60 to intraluminal liner 20, thereby creating an integral composite structure. Such an embodiment is particularly preferred when intraluminal liner 20 is constructed of polytetrafluoroethylene, as discussed above. As such, adhesive 40 extends through pores 25 of the PTFE liner, and bonds to stent 60, thereby providing prosthesis 10 as an integral composite structure which can be effectively mechanically anchored within a body lumen to an intraluminal wall thereof. Such a design overcomes the problems associated with adhering polytetrafluoroethylene with an adhesive material, as discussed above.

Prosthesis 10 is preferably capable of maintaining a blood-tight atmosphere at the time of implantation. In order to control the porosity of prosthesis 10, a natural or synthetic sealant may be incorporated into prosthesis 10, such as a coating or impregnation of tubular body 21 of intraluminal liner 20. Such sealants are well known in the art, and are typically applied to a prosthesis during manufacture and then dried or cured on the prosthesis to provide a sealed, blood-tight graft. For example, intraluminal liner 20 may be a porous structure as discussed above, and may be impregnated with collagen or the like to act as a sealant for rendering prosthesis 10 blood-tight. Such collagen is typically resorbed by the body over time, and is replaced with native tissue, which further serves to anchor prosthesis 10 in place within the body lumen. Moreover, adhesive 40 may include sealing properties and may itself act as a sealant during implantation, thus rendering prosthesis 10 blood-tight.

Prosthesis 10 may further include a removable cover 72 in the form of a sleeve positioned over adhesive 40. Such a sleeve is particularly useful during delivery of prosthesis 10, in that the sleeve prevents adhesive 40 from contacting the luminal surface of the vessel prior to being positioned at the area of implantation.

Figure 6:
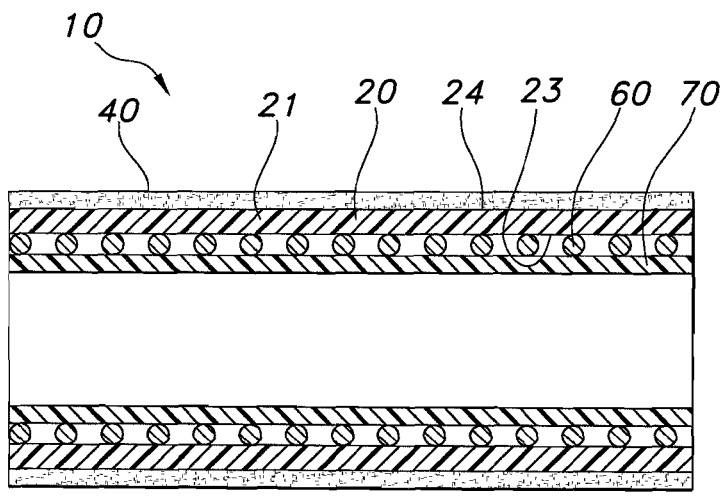
FIG. 6 depicts yet a further embodiment of the present invention including a lumen conduit liner.

As shown in FIG. 6, prosthesis 10 may further include a lumen conduit liner 70 within intraluminal liner 20 for unobstructed blood flow through prosthesis 10. Such lumen conduit liner 70 is particularly preferred in embodiments incorporating a mechanical support such as stent 60. In such embodiments, stent 60 is preferably positioned between intraluminal liner 20 and lumen conduit liner 70. Lumen conduit liner 70 may be constructed of any known material in the art, and is preferably constructed of the same material as intraluminal liner 20. In particularly preferred embodiments, both intraluminal liner 20 and lumen conduit liner 70 are polytetrafluoroethylene. Moreover, adhesive 40 preferably extends through pores of intraluminal liner 60, about stent 60 and through pores lumen conduit liner 70, thereby creating an integral structure for implantation.

Having described the structure of the prosthesis of the present invention in terms of a preferred embodiment, its preferred use in implantation will now be discussed. As is well known in percutaneous applications, a needle is inserted intraluminally into a blood vessel. A guidewire is then inserted through the blood vessel and advanced to the area of implantation of prosthesis 10. A delivery catheter for delivery of prosthesis 10 is then inserted and guided over the guidewire to a position at the area of implantation. Such a delivery catheter is well known in the art, and is preferably in the form of a balloon catheter, with prosthesis 10 including a cover sheath disposed thereover being positioned about the balloon during delivery in a reduced diameter.

After positioning at the area of implantation, the cover sheath is removed from prosthesis 10. The balloon of the delivery catheter is then expanded. Such expansion causes prosthesis 10 to expanded from the reduced, delivery diameter, to an expanded, implantation diameter. Upon contacting of prosthesis 10 with the interior wall surface of the body lumen, adhesive 40 adheres to the wall surface, thus adhering prosthesis 10 to the interior of the body lumen. In embodiments incorporating nodules 50 containing adhesive 40 therein, expansion of the balloon causes engagement of prosthesis 10 against the interior wall surface of the body lumen, which exerts pressure on nodules 50. Such pressure causes nodules 50 to rupture along rupture lines 55, thus causing adhesive 40 contained within nodules 50 to be released and contact the interior wall of the body lumen. As such, prosthesis 10 is adhered to the body lumen.

Further, adhesive 40 preferably extends through pores 25 of intraluminal liner 20, thereby further anchoring tubular body 21 and stent 60 as an integral structure within the body lumen. Expansion of the balloon may exert sufficient pressure to cause additive 40 to flow through pores 25 of intraluminal liner 20, thus effecting such anchoring.

In yet a further embodiment of the present invention, adhesive 40 may be applied to prosthesis 10 in situ after delivery to the site of implantation. For example, intraluminal liner 20 (which may include stent 60) may be delivered to the site of implantation. After expansion of intraluminal liner 20 at the site of implantation, adhesive 40 may be applied to adhere prosthesis 10 to the intraluminal wall of the body lumen. This is preferably accomplished by delivering adhesive 40 through the delivery catheter and applying adhesive 40 to external surface 24 of tubular body 21 of intraluminal liner 20. More preferably, intraluminal liner is a porous structure, and adhesive 40 is applied, for example under pressure, through pores 25 of intraluminal liner 20 from interior surface 23 of tubular body 21 to external surface 24 of tubular body 21. Adhesive 40 may then be cured in situ, thereby firmly attaching prosthesis 10 to the intraluminal wall of the body lumen. In such an embodiment, a multi-channel balloon delivery catheter such as that disclosed in U.S. Pat. No. 5,254,089 is particularly useful.

Various other modifications to the foregoing disclosed embodiments will now be apparent to those skilled in the art. Thus, the particularly described preferred embodiments are intended to be illustrative and the present invention is not meant to be limited thereto. The true scope of the invention is set forth in the following claims.

What is claimed is:

1. An implantable prosthesis comprising:
    a biocompatible elongate liner having an interior surface and an exterior surface and a plurality of pores sufficient to permit ingrowth of body tissue;
    at least one encapsulated biocompatible adhesive disposed on said interior surface of said liner; and
    a mechanical support;
    wherein said adhesive extends through the pores of said liner and is active in an intraluminal environment so as to anchor said liner to an intraluminal surface of a body lumen;
    and wherein said mechanical support is bioabsorbable.

2. The prosthesis of claim 1, wherein the adhesive comprises a member selected from the group consisting of bioabsorbable adhesives, curable polymer adhesives, temperature curing adhesives, pressure sensitive adhesives, and combinations thereof.

3. The prosthesis of claim 2, wherein the curable polymer adhesive is a photodynamically cured adhesive.

4. The prosthesis of claim 1, wherein the adhesive is selected from the group consisting of polyurethanes, cyanoacrylates, silicones, (meth)acrylates, and combinations thereof.

5. The prosthesis of claim 1, wherein the adhesive is a biological sealant capable of bonding the liner to the intraluminal surface of the body lumen.

6. The prosthesis of claim 5, wherein the biological sealant is selected from the group consisting of fibrin, collagen, poly (L-glutamic acid), gelatin based hydrogel, N-vinyl pyrrolidone, and mixtures and combinations thereof.

7. The prosthesis of claim 1, wherein said at least one encapsulated bio compatible adhesive is frangible.

8. The prosthesis of claim 1, wherein said adhesive also bonds said mechanical support to said liner.

9. The prosthesis of claim 1, wherein said liner comprises a member selected from the group consisting of an extruded tube, a polymeric sheet, and a textile tubular body.

10. The prosthesis of claim 9, wherein said textile tubular body is woven, knitted or braided.

11. The prosthesis of claim 1, wherein said liner is in the form of a spun filament tubular body.

12. The prosthesis of claim 1, wherein said liner is formed from a material selected from the group consisting of polyesters, polypropylenes, polyethylenes, polyurethanes, polytetrafluoroethylenes, poly-alpha-hydroxy-acids, and combinations thereof.

13. The prosthesis of claim 12, wherein said liner is formed from expanded polytetrafluoroethylene.

14. The prosthesis of claim 1, wherein said liner is expandable from an insertion diameter to an implantation diameter which is greater than said insertion diameter.

15. The prosthesis of claim 14, wherein said implantation diameter is conformable to the intraluminal surface of a body lumen.

16. The prosthesis of claim 1, wherein said prosthesis further comprises a removable cover.

17. The prosthesis of claim 16, wherein said cover is in the form of a sleeve.

* * * * *